United States Patent [19]

Redus

[11] Patent Number: 5,031,466

[45] Date of Patent: Jul. 16, 1991

[54] METHOD AND APPARATUS FOR DETERMINING STEAM QUALITY AND MASS FLOW RATE

[75] Inventor: Clifford L. Redus, Katy, Tex.

[73] Assignee: Texaco Inc., White Plains, N.Y.

[21] Appl. No.: 529,293

[22] Filed: May 29, 1990

[51] Int. Cl.⁵ .......................... G01F 1/34; G01F 1/74
[52] U.S. Cl. ................................ 73/861.04; 73/29.03
[58] Field of Search ............... 73/29.01, 29.03, 861.03, 73/861.04, 861.61

[56] References Cited

U.S. PATENT DOCUMENTS

| | | | |
|---|---|---|---|
| 4,562,744 | 1/1986 | Hall et al. | 73/861.61 |
| 4,681,466 | 7/1987 | Chien et al. | 73/861.04 |

*Primary Examiner*—Herbert Goldstein
*Attorney, Agent, or Firm*—Jack H. Park; Kenneth R. Priem; Russell J. Egan

[57] ABSTRACT

Steam quality, namely the mass of steam vapor divided by the total mass of water and steam vapor, is determined by measuring the degree of fluctuation of the differential pressure signal across the orifice of a single sharp-edged orifice plate in the steam carrying pipe. The steam quality is inversely related to this measured degree of differential pressure fluctuation.

5 Claims, 2 Drawing Sheets

FLUCTUATIONS IN SYSTEM
PRESSURE OF TEST SECTION

MEASURED VERSUS
PREDICTED STEAM QUALITY

METHOD AND APPARATUS FOR DETERMINING STEAM QUALITY AND MASS FLOW RATE

BACKGROUND OF THE INVENTION

1. The Field of the Invention

This invention concerns a method and apparatus for determining the quality and mass flow rate of a saturated steam flow by measuring pressure fluctuation across an orifice plate. In particular, it relates to a method and apparatus which recognizes the fact that steam quality in a line is inversely related to the degree of fluctuation of the differential pressure signal across the orifice and utilizes this relationship to determine steam quality.

2. The Prior Art

Steam flooding has become an accepted practice for recovery of petroleum products from marginal fields or reservoirs that require a degree of stimulation to produce a satisfactory flow of crude petroleum. There is a need for a simple method and apparatus to determine the quality of saturated steam at the wellhead of an injection well sending steam to such reservoirs. Such a measurement, if simplified, would be particularly useful in determining the amount of heat which is applied to the underground reservoir by the injected steam.

The measurement or monitoring of steam quality is important since the steam's quality and thereby its reservoir or formation heatup effect directly affects the resulting production operations. Further, the quality of the steam which can be most economically injected into a particular substrate or reservoir is contingent on a number of circumstances. The latter include the depth of the reservoir and the anticipated prospects for extracting commercially justified amounts of hydrocarbon products therefrom.

In brief, it is desirable that the quality of steam, that is the mass of the steam vapor divided by the total mass, and the mass flow rate, which is injected into each injection well be altered or adjusted to a level of quality that best conforms to the condition of the formation penetrated by that well. Clearly the quality of the steam and the mass flow rate must be known before any alteration or adjustment can be made.

It is known that in order to be particularly effective in this type of enhanced recovery operation (EOR), the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source, the effectiveness of the insulation on the pipes and joints, and local weather including ambient temperature and wind velocity. It will further depend on the pipe layout including number and orientation of fittings, such as Tees, through which the steam has to travel prior to reaching the injection port or well because of phase separation that can occur in these fittings.

It is important, therefore, as a matter of economic practicality that a flow monitoring and controlling means be instituted into the steam pipeline immediately upstream of each injection wellhead. In many steam flood operations, a choke mechanism in the steam line will function to constrict the steam flow to thereby allow regulation of the steam mass flow rate which enters that particular well.

In my prior U.S. Pat. No. 4,836,032, I disclosed the use of an orifice plate in series with a critical flow choke to provide a method of measurement for both steam quality and mass flow rate. Either the orifice plate or the choke alone can be used to measure steam quality and mass flow rate. However, a mathematical expression for steam quality through both devices is obtained by solving an independent mass flow rate equation for each device, an equation for wet steam through the critical flow choke and an equation for wet steam through a sharp-edged orifice plate. The present invention is distinguished from my earlier invention by the fact that the earlier invention requires two measurements, namely pressure at the entrance to the flow choke and the differential pressure across the orifice plate. The present invention uses the instantaneous differentiating pressure to calculate two parameters, namely, the average differential pressure and a fluctuation parameter that is related to steam quality.

BRIEF SUMMARY OF THE INVENTION

The present invention concerns a method and apparatus for measuring steam quality (mass of steam vapor divided by the total mass of water and steam vapor) of saturated steam. The invention comprises, in brief, a method and apparatus to determine the quality of product stimulation wet steam which is to be injected into a well for producing hydrocarbon products from a heavy oil reservoir being steamflooded for secondary oil recovery. The method is based on the determination of certain characteristics of steam at the injection wellhead. Knowing these characteristics will permit the desired quality determination to be made and, therefore, appropriate adjustments of the steam quality for efficient oil recovery. More precisely, the method and apparatus of the present invention are addressed to measuring steam quality and mass flow rate into a hydrocarbon-containing substrate by means of an injection well.

Stated in a another way, in any process involving steam injection for a secondary oil recovery procedure, a persistent problem exists in making a rapid and accurate determination of the quality and mass flow rate of steam being injected into an individual well or a group of wells. Such knowledge is relevant to production efficiency because the steam quality and mass flow rate directly affect the production operation at the production well and consequently, the investment requirements for similar steam flooding projects.

It is known to be desirable, and highly practical from an economic consideration, to mix saturated water with a high quality steam for achieving a lower but adequate quality saturated steam at each specific wellhead. In such an instance the present invention provides for a means and method to quickly and accurately determine the quality of the steam and its mass flow rate.

It has been determined, for instance, that approximately 20,000 barrels of oil a day must be burned to generate sufficient high-quality wet steam for the production of hydrocarbons in a typical secondary oil recovery from a field. The cost efficiency of this type of steam flood operation can be improved noticeably by economizing the distribution of the steam. This economizing requires an accurate measurement of steam quality and mass flow rate.

Steam quality tapering, and conversion to hot water floods at various field well patterns, have mandated the accurate measurement of steam quality and mass flow rates at individual injection wells. Also, the phenomena of two-phase flow in conduits, as well as phase splitting, have caused steam qualities and mass rates at injection wells to be greater or less than the desired qualities necessary for effective reservoir management.

It is therefore an object of the present invention to provide a method and apparatus for determining the quality of steam which is injected into a steam injection wellhead. Once the wellhead steam quality has been determined with this device, conventional heat loss or pressure drop calculations can be used to determine reservoir sand face conditions.

It is a further object to provide a method and apparatus for readily determining at the wellhead the quality and mass flow rate of wet steam being injected therethrough into a hydrocarbon producing reservoir whereby the hydrocarbon production efficiency is improved.

It is a still further object to provide means for measuring the quality and adjusting the flow rate of steam, under critical flow, which is injected into a hydrocarbon-producing substrate by way of a critical flow choke which regulates steam flow entering the injection well given a measured steam quality.

BRIEF DESCRIPTION OF THE DRAWINGS

The present invention will now be described, by way of example, with reference to the accompanying drawings in which.

DETAILED DESCRIPTION OF THE PREFERRED EMBODIMENT

Figure 1:
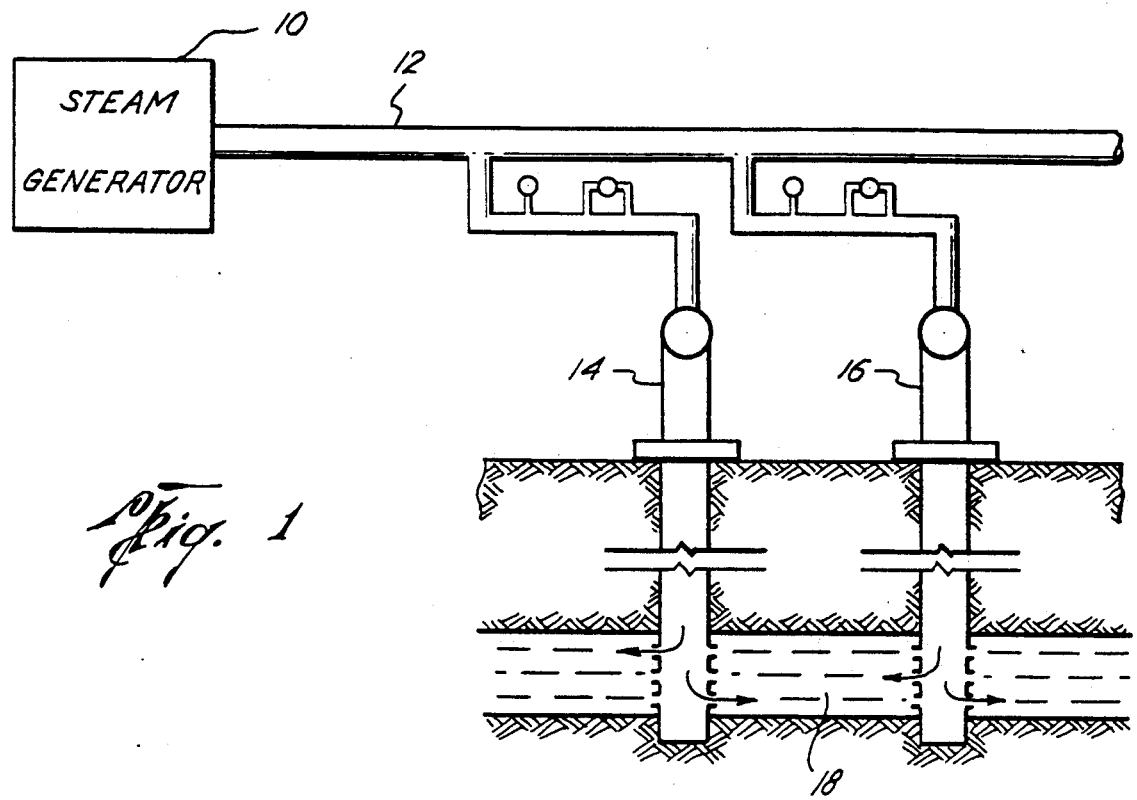
FIG. 1 is a schematic representation of the present invention incorporated into a steam line distribution system in a typical steam flood, secondary recovery operation.

The present invention, with reference to FIG. 1, relates to a method and apparatus for determining the quality and mass flow rate of a steam flow. This determination is usually made immediately prior to the steam being injected into a hydrocarbon containing reservoir. The steam is produced by generator 10 and fed by a series of conduits 12 to individual injection wellheads 14, 16 for injection into a substrate 18. It is readily appreciated that the steam coming from the generator 10 will deteriorate in quality as it passes through the conduits 12, particularly as the steam loses heat and when the steam encounters a pipe Tee (not shown) which directs the steam flow into multiple lines. As the steam travels through the conduits 12, there is the general tendency to form an annular flow with the liquid phase being adjacent to the walls of the conduit and the gaseous phase following generally axially along the conduit. This flow pattern will be disrupted by almost every encounter with a joint or fitting of the conduit, particularly pipe Tees. The mixture of the liquid and vapor phases thus is largely determined by the distance traveled between generator and wellhead, the insulation on the conduit, the weather conditions including ambient temperature and wind velocity and the path or route taken by this steam insofar as they cause a change in steam quality to occur.

Figure 2:
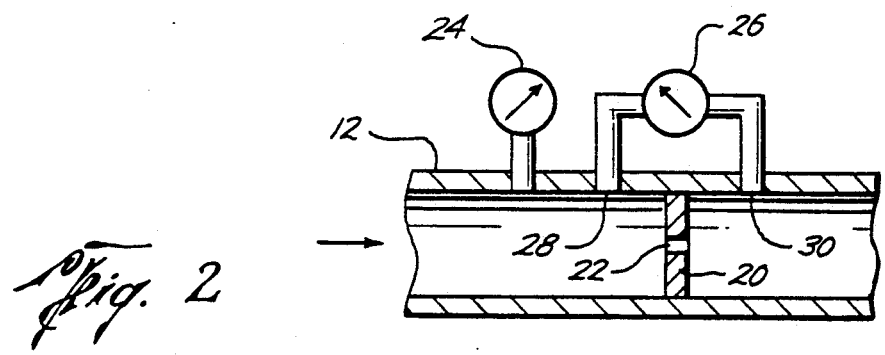
FIG. 2 is a sectional through a single steam quality measuring apparatus according to the present invention.
Figure 3:
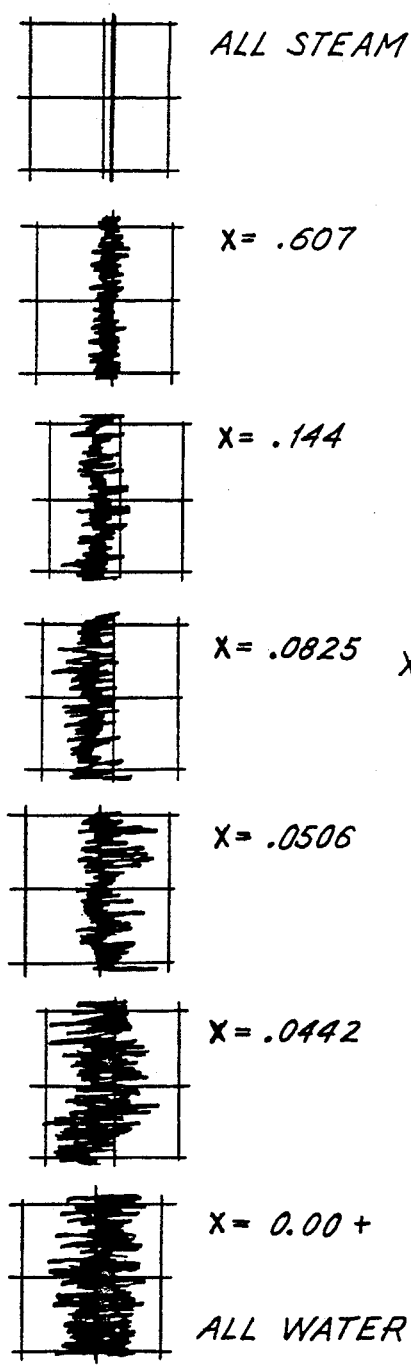
FIG. 3 is a series of segments from a strip chart showing the increased fluctuations detected with increasing wetness of the steam.

Referring to FIG. 2, the conduit 12 is furnished with a sharp-edged orifice plate 20 having a central flow passage or port 22 of sufficient diameter to constrict the pressurized steam but not to the degree that critical flow occurs. Static steam pressure meter 24 is located in the conduit upstream of the plate 20 and differential pressure-reading meter 26 is positioned in the conduit with openings 28, 30 on opposite sides of the orifice plate 20, as defined by standard orifice metering practice.

The combination of the static and differential pressure reading are employed by means 25 for determining steam qualify and the mass flow rate at injection wellheads.

Referring back to FIG. 1, the normally insulated steam flow pipeline on conduit 12 includes fittings, couplings, flanges and the like (all of which are known and none of which have been shown for the sake of simplicity of the drawings) into which a flow of steam is directed from a pressurized source, namely the generator 10, to the wellheads. Steam at the injection wellhead typically has a quality between 10 and 80 percent and a mass flow rate from 100 to 600 barrels of steam per day cold water equivalent (BSPD-CWE) and at a pressure between 300 and 700 psig. Even though the empirical correlation was tested over these operating conditions, the device will work over flow rate ranges from 50 to 5000 BSPD-CWE and pressures from 100 to 2000 psig with appropriate modification of the empirical constants. The function of the aperture plate in this type of steam injection operation is to constrict the flow of steam passing therethrough to a reduced diameter to thereby cause a pressure drop which can be related to the volumetric flow rate in the line. Operationally as the steam issues from the high pressure source, it will be of a known quality, depending primarily upon its water content. For example, the greater percentage of water intermixed with the steam vapor, the lesser will be the quality of the saturated steam. Since the steam quality will be subject to reduction in any conduit that carries the hot flow, the conduit is provided with suitable insulation or cover to minimize heat loss through the conduit's metallic walls.

The novelty of the present invention lies in recognition of the fact that steam quality in the line is inversely related to the degree of fluctuation of the differential pressure signal across the orifice of a single sharp-edged orifice plate and that this relationship can be used to determine steam quality. In other words, at high steam qualities there is very little fluctuation in the differential pressure across the orifice plate while there is a large fluctuation of the differential pressure at low steam qualities. The degree of fluctuation is related to the relative volume of water and steam in the line. It has been noted, that the fluctuations increased with decreasing steam quality. In order to use this phenomenon to determine steam quality, first an empirical equation must be developed that gives steam quality as a function of some measure of the differential pressure fluctuation. Once the steam quality in the line is measured using this equation, the mass flow rate can be determined from an existing wet steam orifice plate equation such as the James equation.

For example, let the fluctuation parameter be defined as $$\zeta = \frac{\sqrt{\frac{n \sum_{i=1}^{n} \phi_i^2 - \left[\sum_{i=1}^{n} \phi_i\right]^2}{n(n-1)}}}{\frac{1}{n} \sum_{i=1}^{n} \phi_i} \qquad (1)$$

where $\phi_i$ is the ith instantaneous differential pressure measurement, and n is the number of instantaneous differential pressure measurements that the average is running over. $\zeta$ is then the standard deviation of the instantaneous differential pressure divided by the mean of the instantaneous differential pressure over an interval of time. With this defined fluctuation parameter $\zeta$, a relationship between steam quality X and $\zeta$ is defined as $$X = a\zeta^b \qquad (2)$$

where X is the no slip or homogeneous steam quality and a and b are empirical constants to be derived from a field test. Once the steam quality is determined from the equations (1) and (2), the mass flow rate through the orifice plate can be determined from the James equation as $$W = \frac{24.65 \, C_o d}{\sqrt{1 - \beta^4}} \sqrt{\frac{\phi}{X^{1-5}v_{fg} + v_f}} \qquad (3a)$$

where $$C_o = 0.61, \qquad (3b)$$

$$\phi = \frac{1}{n} \sum_{i=1}^{n} \phi_i, \qquad (3c)$$

and $$\beta = \frac{d}{D}, \qquad (3d)$$

and where the specific volumes, in ft$^3$/lbm$_m$, are determined from Chien as $$v_{fg} = \begin{cases} 407.255_p^{-0.9825} & \text{for } 100 < p < 500 \text{ psia} \\ 778.702_p^{-1.0868} & \text{for } 500 < p < 900 \text{ psia} \end{cases} \qquad (4)$$

$$v_f = \begin{cases} 0.316 p^{0.5765} & \text{for } 100 < p < 300 \text{ psia} \\ 0.000004(p + 4425) & \text{for } 300 < p < 800 \text{ psia} \\ 0.0000035(p + 5171.4) & \text{for } 800 < p < 1000 \text{ psia} \end{cases} \qquad (5)$$

To validate this concept, a field test was conducted at Texaco's Kern River Field. Table 1 shows a sample of the field results from using a one inch orifice plate. In this test a 12 MM Btu/hr portable steam generator supplied steam to a 2 inch schedule 40 test section. Shown in Table 1 are the static and differential pressures, the measured fluctuation parameter as defined by equation (1) with n=50 point averaging over a 30 second time span for each test point. Also shown are the average measured steam quality and the steam quality predicted from equations (1) and (2).

TABLE 1

FIELD TEST RESULTS

| Pressure (psig) | Measured Diff. Pres. (In water) | Measured Steam Qual. (%) | Measured Mass Rate (bwpd-cwe) | $\zeta$ (—) | Predicted Steam Qual. (%) | Predicted Rate (bwpd-cwe) |
|---|---|---|---|---|---|---|
| 513 | 104 | 44.1 | 300.1 | 0.075 | 43.6 | 301.3 |
| 522 | 111 | 48.7 | 291.8 | 0.047 | 50.2 | 284.5 |
| 508 | 110 | 45.9 | 299.2 | 0.049 | 49.6 | 281.7 |
| 515 | 112 | 47.2 | 297.3 | 0.036 | 54.4 | 268.1 |
| 507 | 111 | 45.7 | 300.8 | 0.041 | 52.3 | 272.3 |
| 619 | 157 | 64.6 | 308.9 | 0.022 | 63.1 | 313.9 |
| 621 | 160 | 65.6 | 308.9 | 0.020 | 64.9 | 311.1 |
| 629 | 164 | 68.9 | 304.0 | 0.021 | 64 | 320.2 |
| 621 | 163 | 65.6 | 311.2 | 0.019 | 65.9 | 310.6 |
| 615 | 162 | 65.4 | 310.0 | 0.020 | 64.9 | 311.5 |
| 667 | 192 | 80.0 | 304.0 | 0.010 | 79.7 | 305.3 |
| 661 | 191 | 78.8 | 304.9 | 0.010 | 79.7 | 303.1 |
| 650 | 187 | 73.1 | 315.5 | 0.012 | 75.7 | 308.5 |
| 655 | 183 | 72.7 | 314.9 | 0.014 | 72.3 | 316.6 |
| 647 | 181 | 70.7 | 317.6 | 0.015 | 70.8 | 317.6 |
| 453 | 35 | 30.0 | 215.7 | 0.288 | 29.1 | 216.7 |
| 450 | 34 | 29.5 | 215.5 | 0.400 | 26.4 | 227.1 |
| 456 | 34 | 31.5 | 207.9 | 0.346 | 27.5 | 222.5 |
| 455 | 34 | 31.1 | 208.6 | 0.333 | 27.8 | 220.7 |
| 443 | 33 | 28.2 | 216.8 | 0.274 | 29.5 | 206.3 |

A regression analysis of the data in Table 1 give the coefficients in equation (2) of $$a = 0.20 \qquad (6a)$$

$$b = -0.301 \qquad (6b)$$

Figure 4:
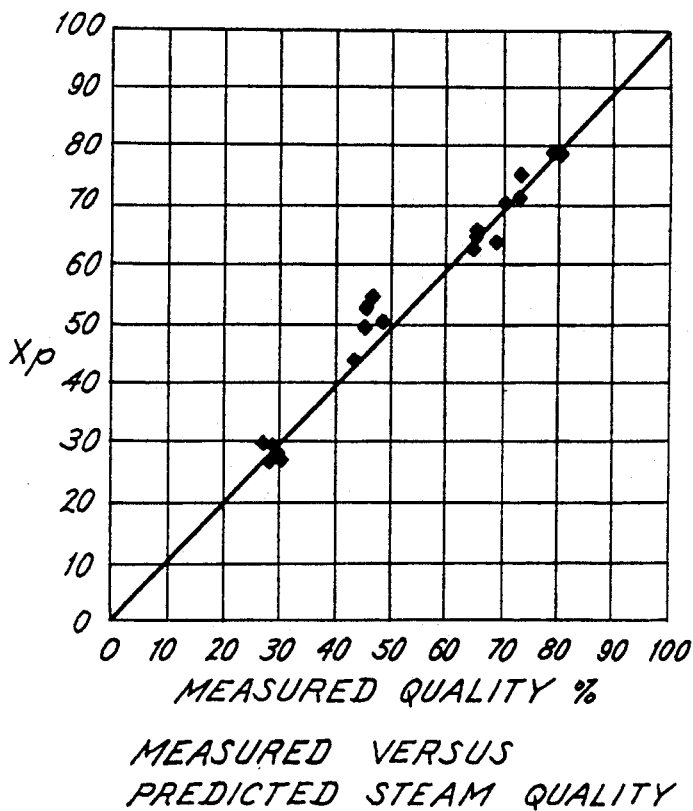
FIG. 4 is a graph showing measured versus predicted steam quality.

FIG. 4 shows measured versus predicted steam quality using equations (2) and (6).

The present invention may be subject to various changes and modifications without departing from the spirit or essential characteristics of the invention. Thus, the embodiment described should be considered in all respects as illustrative and not restrictive as to the scope of the invention which is defined by the appended claims.

What is claimed is:

1. An apparatus for determining steam quality and mass flow rate in a saturated steam line, comprising:
    a single orifice plate fixedly mounted transversely across a saturated steam line;
    means for measuring static pressure upstream of said orifice plate;
    means for measuring the differential pressure across the orifice plate;
    means to derive a fluctuation parameter based upon said measured differential pressure; and
    means to calculate both saturated steam quality and mass flow rate based on the measured fluctuations and static pressure used in specific volume calculations determined from a known wet steam orifice plate equation.

2. The apparatus according to claim 1 where steam quality is determined from the equation $$X = a\zeta^b,$$

where the fluctuation parameter is defined as $$\zeta = \frac{\sqrt{\frac{n \sum_{i=1}^{n} \phi_i^2 - \left[\sum_{i=1}^{n} \phi_i\right]^2}{n(n-1)}}}{\frac{1}{n}\sum_{i=1}^{n} \phi_i}$$

and the coefficients a and b are $a = 0.20,$ $b = -0.301.$

3. The apparatus according to claim 1, wherein the mass flow rate through the orifice plate is determined from wet steam orifice correlation $$W = \frac{24.65 \, C_o d}{\sqrt{1-\beta^4}} \sqrt{\frac{\phi}{X^{1-5} v_{fg} + v_f}}$$

where $C_o = 0.61$ and where the measured static pressure is used to determine the water and steam vapor specific volumes.

4. The apparatus according to line 1 wherein said apparatus is operated at subcritical flow conditions.

5. A method for determining steam quality and mass flow rate in a wet steam line comprising the steps of
measuring differential pressure across an orifice plate; and
measuring static pressure in said line and utilizing this measurement for specific volume calculations upstream of a sharp-edged orifice plate;
utilizing fluctuation, which is a derived parameter based upon measured differential pressure, to calculate steam quality and determining mass flow rate from a known wet steam orifice plate equation.

* * * * *